(12) United States Patent
Sontrop et al.

(10) Patent No.: US 8,515,681 B2
(45) Date of Patent: Aug. 20, 2013

(54) CLASSIFICATION OF SAMPLE DATA

(75) Inventors: Herman Sontrop, Eindhoven (NL); Wilhelmus Franciscus Johannes Verhaegh, Eindhoven (NL); Rene Van Den Ham, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 348 days.

(21) Appl. No.: 12/988,540

(22) PCT Filed: Apr. 21, 2009

(86) PCT No.: PCT/IB2009/051628
§ 371 (c)(1),
(2), (4) Date: Oct. 19, 2010

(87) PCT Pub. No.: WO2009/130663
PCT Pub. Date: Oct. 29, 2009

(65) Prior Publication Data
US 2011/0040491 A1 Feb. 17, 2011

(30) Foreign Application Priority Data
Apr. 25, 2008 (EP) .................................... 08155148

(51) Int. Cl.
*G01N 33/48* (2006.01)
(52) U.S. Cl.
USPC ........................................................ 702/19
(58) Field of Classification Search
USPC ............................................................ 702/19
See application file for complete search history.

(56) References Cited

PUBLICATIONS

Van De Vijver et al: "A Gene-Expression Signature as a Predictor of Survival in Breast Cancer"; The New England Journal of Medicine, Dec. 2002, vol. 347, No. 25, pp. 1999-2009.
Weng et al: "Rosetta Error Model for Gene Expression Analysis"; Bioinformatics, 2006, vol. 22, No. 9, pp. 1111-1121.
Marchal et al: "Computational Biology and Toxicogenomics"; Chapter 3 of the Book, "Predictive Toxicology"; pp. 37-92, Edited by Christoph Helma, CRC Press, 2005.
Kerr et al: "Bootstrapping Cluster Analysis: Assessing the Reliability of Conclusions From Microarray Experiments"; Proceedings of the National Academy of Science (PNAS), Jul. 2001, vol. 98, No. 16, pp. 8965-8965.
Yeung et al: "Multiclass Classification of Microarray Data With Repeated Measurements: Application to Cancer"; Genome Biology, 2003, vol. 4, No. 12, pp. R83-R83.19.
Yeung et al: "Clustering Gene-Expression Data With Repeated Measurements"; Genome Biology, 2003, vol. 4, Issue 5, pp. R34-R34.17.
Van T'Veer et al: "Gene Expression Profiling Predicts Clinical Outcome of Breast Cancer"; Nature, Jan. 2002, vol. 415, pp. 530-535.

*Primary Examiner* — Jerry Lin (57) ABSTRACT

A classification system (100) for classification of bio molecular data is provided. An input of the system receives a plurality of features (102) of a sample to be classified and a plurality of respective error estimates (104). A statistical module (106) associates probability density functions (108) with the features, wherein variances of the probability density functions depend on the error estimates. A replication module (110) produces a plurality of perturbed replicas (112) of the sample, wherein the features are randomly perturbed according to the corresponding respective probability density functions. A classifier (114) classifies the perturbed replicas based on the perturbed features. An analyzer (118) classifies the sample to be classified based on a statistical analysis of the classified replicas (116) to obtain a sample classification (120).

20 Claims, 4 Drawing Sheets

CLASSIFICATION OF SAMPLE DATA

FIELD OF THE INVENTION

The invention relates to classification, in particular to classifying samples involving noisy measurement data. More particularly, the invention relates to classifying biomolecular data.

BACKGROUND OF THE INVENTION

In the area of molecular diagnostics, microarray data and proteomics data are increasingly being used to develop new tests for classifying patients. An example of such a test is described in "Multiclass classification of microarray data with repeated measurements: application to cancer" by K. Y. Yeung and R. E. Bumgarner, in Genome Biology, 2004, 4:R83.

Classification of microarray data and proteomics data may relate to, for example, diagnosis and patient stratification. Finding the right biomarkers, for example the right set of genes or proteins, to base this classification on, and finding the right rule to translate the measurements of these biomarkers into a classification, is of prime importance, as it may have a large impact on the classification accuracy. Given the biomarkers and the classification rule, new cases can be classified in a clinical setting or at a general practitioner.

Microarrays offer an important tool to biologists by facilitating the ability to simultaneously measure thousands of gene expression levels per sample. One of the main tasks of microarray classification is to map a set of gene expression measurements, the features, to a given target label, i.e. a patient's class. In contrast to measuring a person's body temperature or a person's height, measuring gene expression levels is very challenging, costly and time consuming. It is a multi-step process in which many individual procedures have to be performed. Some of these steps involve conditions that cannot be fully controlled and may cause the classification result to be unreliable.

SUMMARY OF THE INVENTION

It would be advantageous to have an improved classification of biomolecular data. To better address this concern, in a first aspect of the invention a classification system is presented that comprises an input for receiving measurement data, comprising measurements of a plurality of numerical features of a sample to be classified and a plurality of respective error estimates of respective ones of the plurality of numerical features;

a statistical module for associating respective probability density functions with the respective ones of the plurality of numerical features, wherein the respective probability density functions depend on the respective error estimates of the respective numerical features;

a replication module for producing a plurality of perturbed replicas of the sample, the perturbed replicas comprising perturbed features, wherein the respective ones of the plurality of numerical features are randomly perturbed according to the corresponding respective probability density functions to obtain the perturbed features;

a classifier for classifying respective ones of the plurality of perturbed replicas based on the perturbed features and by applying predetermined classification criteria to obtain classified replicas, wherein each classified replica has a class associated therewith;

an analyzer for classifying the sample to be classified based on a statistical analysis of the classified replicas to obtain a sample classification.

Because the numerical features of the replicas are perturbed, the classification will in general not always be the same for all replicas. Moreover, since the features of the replicas are perturbed according to the probability distribution attributed to the noise that is present in the measured features, the number of replicas classified as being of a particular class is related to the probability or likelihood that the sample to be classified is of that particular class in view of the noise. Consequently, the analyzer can take this probability into account to provide an improved classification and/or to provide more insight in the reliability of the classification.

Preferably, the statistical module varies a variance in dependence on the error estimates, for example proportionally to the error estimates.

For example, the analyzer assigns the class having the highest probability or likelihood to the sample. This improves the accuracy (e.g. specificity and/or sensitivity) of the classification.

Preferably, the analyzer is arranged for computing a value indicative of a likelihood that the sample belongs to a particular class. This gives the user of the classification system an indication which he can use to decide whether he can rely on the classification. The likelihood may be indicated, for example, by means of a probability value or a p-value of a statistical hypothesis test.

Preferably, a plurality of likelihood values is computed, wherein each respective likelihood value is indicative of a probability or likelihood that the sample belongs to a respective particular class. This allows the user to get a better understanding of the possible classes to which the sample may belong, which may be used to decide whether additional diagnoses are required.

To obtain a good classifier, the classifier may be trained using a training data set that comprises a plurality of perturbed replicas of each sample.

Other aspects of the invention are defined in the independent claims. The dependent claims define advantageous embodiments.

BRIEF DESCRIPTION OF THE DRAWINGS

These and other aspects of the invention will be further elucidated and described with reference to the drawing, in which.

DETAILED DESCRIPTION OF EMBODIMENTS

One of the difficulties with molecular measurements such as microarray data, is that they are quite noisy. One of the sources of this noise in microarray data is given by the variation in hybridization. However, a microarray measurement does not only give an indication of the gene expression, but also gives an estimate for the error introduced by, amongst others, the hybridization differences on the array. This error estimate has been used to some extent in the biomarker discovery phase, for example in a pre-filtering step as described in L. J. van 't Veer et al., "Gene expression profiling predicts clinical outcome of breast cancer", in Nature, 415:530-536, 2002 (hereinafter: Van 't Veer et al.).

If the error estimate is not used in the eventual classification, the classification of a new case is only based on the gene expression measurements, not taking into account that these measurements may be very inaccurate.

In an embodiment, a case is not classified just once, based on the actual measurements, but multiple times, where every time perturbation noise is added according to the given error estimate. In more detail this may be performed as follows.

Normally, n genes used in a biomarker and measurements $x_i$ for genes $i=1, \ldots, n$ are given. These gene measurements are used in a classifier, which can be seen as a function $f(\vec{x})$, and which is called once on the data $\vec{x}=(x_1, \ldots, x_n)$ of the case.

If the error estimate of each measurement $x_i$ is denoted by $e_i$, then a new instance $\vec{x}'$ is created by adding perturbation noise to $\vec{x}$. Such a new instance, or replica, is created multiple times (for example 1000 times). If, for instance, the error is normally distributed (as is typically the case in microarray data), and $e_i$ indicates the estimated standard deviation of the measurement, then a new instance is generated by $$x_i' = x_i + N(0, e_i),$$

wherein $N(0, e_i)$, is the normal distribution having a mean of zero and a standard deviation $e_i$. Then the classifier $f$ is applied to each of the replicas to obtain classified replicas. The results of the classified replicas are combined into one outcome. A rule that can be applied for the latter is to use a majority vote, wherein a replica classified with a particular class represents a vote for that class. In addition, one can show how often each vote occurred, to give an indication of the uncertainty introduced by the measurement error. This kind of information can then be used in a clinical decision support system (CDSS) to take into account in the end advice.

These techniques can not only be used on microarray data, but also on other data, as long as an estimate is available for the measurement noise. This noise may be due to technical noise in the microarray experiment, but also for example noise from noise models based on repeated experiments.

When applying the techniques described hereinabove, the measurement error influences the classification outcome, because the techniques do not only use the actual measurements, but also the error estimates. Furthermore, the method can give not just one classification outcome, but also a probability distribution over the different outcomes.

Figure 1:
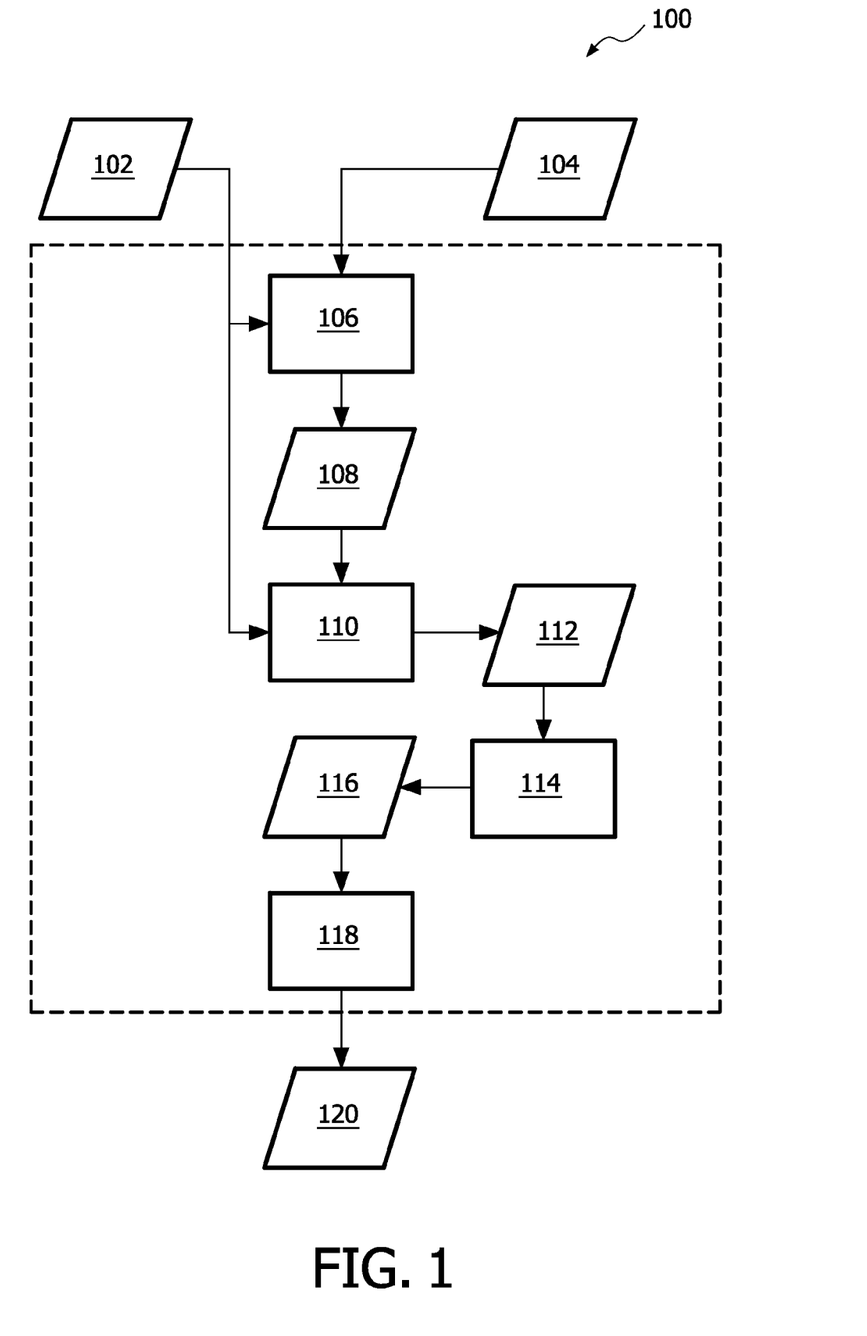
FIG. 1 is a block diagram of a classification system.

FIG. 1 illustrates an embodiment of a classification system 100 for classification of biomolecular data. This classification system 100 has an input for receiving measurement data. The measurement data may comprise, for example, at least one of:
(a) gene expression data,
(b) DNA transcript data (does not only measure gene expression, but also other pieces of DNA which may be expressed in a cell and which may influence the function of a cell), or
(c) proteomics data (e.g. the concentrations of a number of proteins in a sample).

Data types (a) and (b) above may typically be measured using microarrays or assays. Data type (c) may typically be measured using a mass spectrometer. However, other types of measurements may also be used.

The input of the classification system 100 is arranged for receiving measurements of a plurality of features 102 of a sample to be classified. Herein, the features comprise for example the types of data outlined above under (a), (b), and (c). For example, a feature is indicative of a concentration of a particular substance in a sample. A feature may represent to what extent a particular gene or DNA transcript has come to expression. The input of the classification system 100 is also arranged for receiving a plurality of respective error estimates 104 of respective ones of the plurality of features. These error estimates provide an indication of the extent to which a measurement of a feature can be relied upon.

The system 100 comprises a statistical module 106 for associating respective probability density functions 108 with the respective ones of the plurality of features. The probability density functions 108 may represent the probability density function of the measurement error, in which case the probability density function typically has a mean of zero and a variance depending on the error estimate. Alternatively, the probability density functions 108 may represent probability density functions of the features themselves, in which case the mean of such a probability density function typically corresponds to the measurement of the feature and the variance depends on the error estimate of the feature. The general type of the probability distribution underlying the probability density function 108 may be the same for all features. Typically, a normal distribution can be used for the probability density functions, where the variances depend on the respective error estimates 104 and the means are zero (or correspond to the measured feature). However, other probability density functions can be used, in particular when a measurement is known to have an error distribution that is not a normal distribution. In a straightforward implementation of the classification system 100, an independent probability distribution is assumed for each feature, however in a more advanced implementation, the probability density functions may be multivariate and depend on several or all measured features 102 and/or error estimates 104.

The system 100 comprises a replication module 110 for producing a plurality of perturbed replicas 112 of the sample, i.e., perturbed replicas of the plurality of features 102 (and possibly of the plurality of error estimates 104, wherein the error estimates may or may not be perturbed). To produce a perturbed replica, the replication module 110 randomly perturbs the features 102 according to the corresponding respective probability density functions. These respective probability density functions may have different variances based on the error estimates, as associated with the features by the statistical module 106. As discussed above, in a straightforward implementation the probability density functions may all have the same type of distribution (e.g. a normal distribution). The perturbed replicas comprise the perturbed features.

The system 100 comprises a classifier 114 for classifying respective ones of the plurality of perturbed replicas based on the perturbed features. The classifier evaluates the perturbed features of a perturbed replica by applying predetermined classification criteria to obtain classified replicas 116. Many kinds of classifiers are known in the art. A suitable classifier could be, for example, a nearest mean classifier, or a support vector machine.

The system 100 comprises an analyzer 118 for classifying the sample to be classified based on a statistical analysis of the classified replicas 116 to obtain a sample class 120. The statistical analysis performed by the analyzer 118 may comprise a voting system (e.g. the class having the most perturbed replicas becomes the sample classification).

To compute a value indicative of a likelihood that the sample belongs to a particular class, a percentage of the replicas in the sample class can be computed. This gives an indication of the reliability of the sample classification, which may be used by an operator to decide whether additional measurements, or any other diagnostic activities, are necessary in order to obtain a diagnosis with sufficient certainty. The likelihood may be for example a probability or a p-score (confidence measure).

The analyzer 118 may also be arranged to compute a plurality of likelihood values, wherein each respective likelihood value is indicative of a probability, likelihood, or confidence that the sample belongs to a respective particular class. This can be used for example to discover whether one of the classes is much more likely than any other class, or whether two or more classes are approximately equally likely. In the latter case, the outcome may be less reliable, and it is good to know that. Also this makes it possible to rule out one or more of the classes, if it has a very low likelihood.

In a particularly efficient embodiment that still provides good results, the statistical module 106 is arranged for associating normal distributions with a zero mean and standard deviations proportional to the error estimates.

The classifier 114 may be arranged for applying respective weights to respective ones of the plurality of features of individual replicas based on the respective error estimates of the respective features. This way, the influence of features having a larger error estimate is reduced compared to the influence of features having a smaller error estimate. This improves the individual classifications of the perturbed replicas and can be used to reduce the influence of features having a very large error estimate.

For example, suppose the classifier uses a nearest centroid method in which an average profile (centroid) is given for each of the classes. A sample (or, more particularly, a perturbed replica) may be classified by computing the distances to the different centroids and choosing the nearest centroid. Then, if a certain measurement of the patient to be classified is very noisy, the influence of this measurement on the classification can be reduced by modifying the calculation of the distances (e.g. the features can be weighted with a weight that is inversely proportional to the estimated error of the measurement of the feature). If a k-nearest neighbor rule is used, then it is also possible to weight the contribution of a measurement to the used distance measure. This might not only be based on the measurement error of the patient to be classified, but also on the error in the measurements of the 'neighbors'. This can be used on microarray data, but also on other data, as long as an estimate is available for the measurement noise. This not only includes technical noise such as given in microarray experiments, but it can also include noise from noise models based on repeated measurements.

The classification system 100 may be built into a measurement system such as a microarray system or an assay or a mass spectrometer, for example. It may also be implemented as a computer program product to be executed on any suitable processing device, such as a workstation, personal computer, PDA, or the like. Preferably the processing device is coupled to the measurement system via a data link (either a direct link such as USB, or via a network such as ethernet or wireless LAN or the Internet). The results of the analyzer may be displayed on a display of the processing device or on a separate display, it may be printed or passed on to another software module or another device for further processing. For example, the output of the analyzer may be an input of a clinical decision support system. Such a clinical decision support system may produce a diagnosis based on the output of the classification system 100 and any other data that may be available to the clinical decision support system. The output of the analyzer may also be used in a computer aided detection and/or computer aided diagnosis system.

Typically the classifier 114 needs to be trained in order to give reliable classification results. The advantages of for example the perturbed replicas may also be used during the training procedure. To this end, a training data set generator and a training module may be provided. These items are not shown in the drawing. In order to train the classifier 114, the training data set generator generates a training data set. Preferably, the training data set generator is arranged for including a plurality of perturbed replicas in the training data set. For example, it starts with a training data set containing measured features of a plurality of samples. These measured features are obtained from a microassay, for example, and are preferably accompanied by a ground truth classification. The measured features of each sample are replicated a number of times to obtain a plurality of perturbed replicas of each sample. The training module is used to train the classifier using the training data set thus generated. After training, the trained classifier may be used to classify new samples, preferably in conjunction with a set of perturbed replicas of the new sample.

Figure 2:
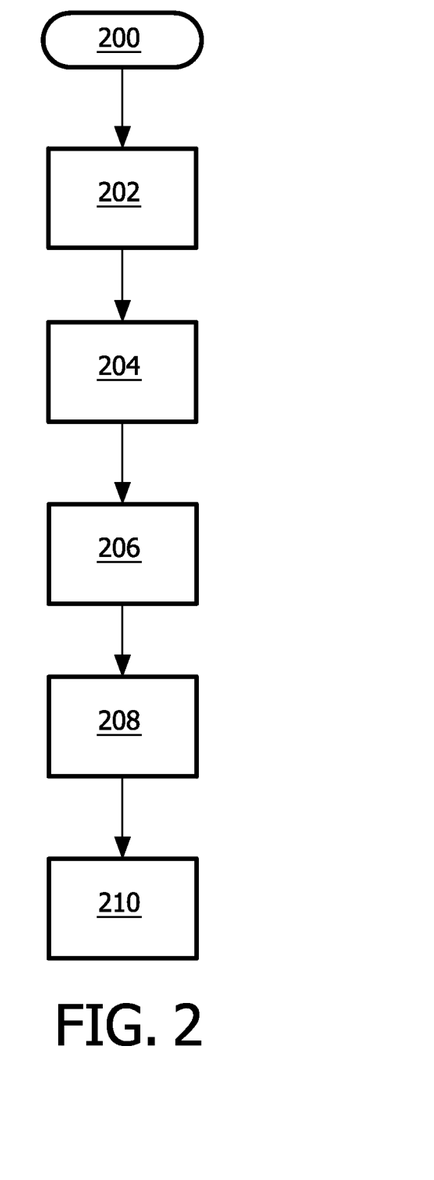
FIG. 2 is a flowchart illustrating processing steps of a classification system.

FIG. 2 illustrates processing steps of a method of classifying biomolecular data. The method is initiated in step 200, for example in response to a user input command. In step 202, the measurement data is received. The measurement data comprises measurements of a plurality of features 102 of a sample to be classified and a plurality of respective error estimates 104 of respective ones of the plurality of features. In step 204, respective probability density functions 108 are associated with the respective ones of the plurality of features. Respective variances of the respective probability density functions depend on the respective error estimates of the respective features. In step 206, a plurality of perturbed replicas 112 of the sample are produced. The perturbed replicas comprise perturbed features. The respective ones of the plurality of features are randomly perturbed according to the corresponding respective probability density functions to obtain the perturbed features. In step 208, respective ones of the plurality of perturbed replicas are classified based on the perturbed features and by applying predetermined classification criteria. This results in classified replicas 116. As a result, each classified replica has a class associated therewith. In step 210, the sample is classified based on a statistical analysis of the classified replicas 116 to obtain a sample classification 120.

Such a method may be implemented by means of an electronic circuit or, preferably, by means of a computer program product comprising machine readable instructions.

Figure 6:
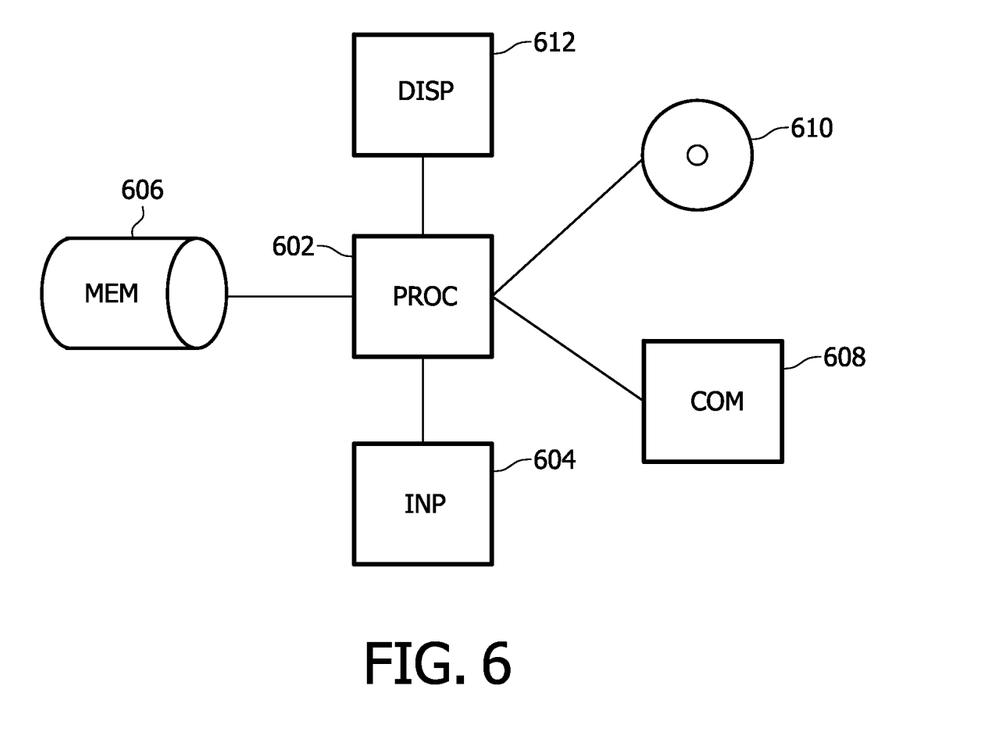
FIG. 6 is a block diagram of a hardware architecture.

FIG. 6 illustrates a hardware architecture suitable for implementing the system of FIG. 1 and/or the method of FIG. 2, as well as other techniques described in this text. The hardware architecture shown is merely an example. The figure shows a processor 602 and a memory 606. A computer program product may be loaded into the memory 606 (for example a ROM or RAM memory), and the processor 602 is arranged to perform the steps defined by means of machine readable instructions and stored in memory 606. The computer program product comprises the machine readable instructions needed for applying one or more of the techniques described in this text. An input 604 can be used to trigger certain activities such as data input, data processing, starting the classification, controlling the visualization and other outputting of the results. A display 612 provides for a way to show the classification results, for example. Communications port 608 may be connected to, for example, a microassay, possibly via a network as described above. The communications port 608 may also be connected to a device that further processes the output of the system 100 or of the method, for example to provide decision support. Alternatively, the data may be provided by means of a removable media device 610 (e.g. a DVD reader or CD-ROM reader or flash memory USB stick). If the removable media device has writing capabilities (e.g. it is DVD+RW compatible, or it is a flash memory USB stick), it is possible to output the final results and/or the intermediate results of the classification system 100 also to the removable media.

Microarrays are an inherently noisy technique with varying degrees of uncertainty in its individual measurements. The degree of uncertainty in a microarray measurement can be quantified via noise models, which attempt to quantify the different sources that disturb the measurement process. They provide information on the variability of the microarray measurements, for instance in the form of confidence intervals or P-values. This information may be propagated into the determination of differential expression or clustering tasks. However, the variability information may also be used in classification problems. Such feature noise has an impact on feature selection and classification.

Microarrays may measure gene expressions indirectly via hybridization intensity measurements. The measured hybridization intensity is approximately proportional to the mRNA abundance in a sample. Probably the most important use of these measurements is to study changes in gene expression under different conditions. In two-color arrays, two mRNA sources are competitively hybridized to the same array. Per probe, two intensity measures $I_1(i,j)$ and $I_2(i,j)$ are obtained, where i is the index of the microarray and j represents the 'gene' or targeted sequence. Often, one is interested in the log ratio of the intensity measurements, given by $$x_{ij} = \log_{10}\left(\frac{I_2(i, j)}{I_1(i, l)}\right).$$

The ratio $$\frac{I_2(i, j)}{I_1(i, j)}$$

is called a fold-change. Note that when both intensities are equal, $x_{ij}$ is zero. A non-zero log ratio reflects a change in measured intensity between the individual intensities. For instance, a log ratio of 2 implies that the intensity $I_2$ was $10^2=100$ times higher than the intensity $I_1$. Taking the logs of these fold-changes has several advantages as it tends to symmetrize the otherwise more skewed intensity distributions and it treats up and down regulation similarly e.g.

$$\left|\log_{10}\left(\frac{1000}{10}\right)\right| = \left|\log_{10}\left(\frac{10}{1000}\right)\right|.$$

As stated earlier, individual microarray intensity measurements are very noisy. So-called error models provide to each intensity measurement an estimate on its variability. As a result, the feature values $x_{ij}$ will be stochastic as well.

Data sets that were used in two earlier studies are used to evaluate the performance of the techniques disclosed herein. Both studies deal with groups of female patients who all developed breast cancer. The aim in Van 't Veer et al. was to determine a gene expression signature, assumed to be present in removed tumor tissue, that could be used to predict whether or not a patient would develop distant metastasis within 5 years. These patients were so-called lymph-node negative, i.e., they had no tumor cells in their local lymph nodes at diagnosis.

The data of Van 't Veer et al. contained a training set of 78 patients and a validation set of 19 patients. The other dataset was described in "A gene-expression signature as a predictor of survival in breast cancer" by Van de Vijver et al., in New England Journal of Medicine, 347(25):1999-2009, December 2002, Evaluation Studies (hereinafter: Van de Vijver et al.). Van de Vijver et al. treats a cohort of 295 patients that were used to further validate the prognostic value of the signature as derived in Van 't Veer et al. Both studies used the same microarrays and protocols and hence the data may be pooled. In the present study the data of both studies were combined into a training set of 78 patients and a validation set of 106. Noteworthy is that Van de Vijver et al. contains both lymph-node negative (151) and lymph-node positive patients (144). The patient groups in Van 't Veer et al. and Van de Vijver et al. overlap as the cohort of 295 cases contains 61 of the training and 3 of the validation cases also present in Van 't Veer et al. In order to obtain a homogeneous population only the lymph-node negative cases are considered. The original validation set of 19 cases was extended with an additional 151−(61+3)=87 cases. This provides a larger validation set containing in total 19+87=106 cases.

Figure 3:
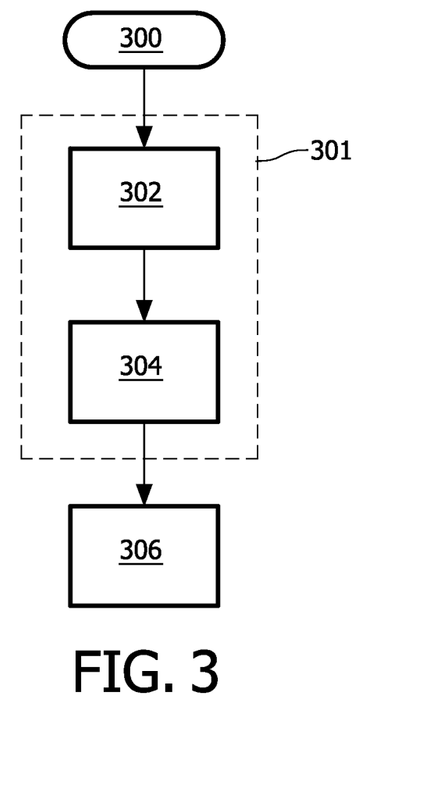
FIG. 3 is a flowchart illustrating a basic process of training a classifier and performing a classification with the trained classifier.

FIG. 3 illustrates a basic process of training a classifier and performing a classification with the trained classifier. In step 300, the process is initiated. Block 301 (which contains steps 302 and 304) indicates the steps involved in training the classifier. Step 306 illustrates performing a classification with the trained classifier. In step 302, a training data set is provided as follows, for training the classifier. Let $I^g$ denote a set of $n_g$ patients belonging to a good prognosis class and $I^p$ denote a set of $n_p$ patients belonging to a poor prognosis class. The class label of patient i is denoted by $L_i$. In step 304, the average good profile $x^g$ and the average poor profile $x^p$ are computed. Denote with $x_i$ the vector containing the expression levels of patient i. The average good profile $x^g$ and the average poor profile $x^p$ are defined as $$x_j^g = \frac{1}{n_g}\sum_{i \in I^g} x_{ij} \text{ and } x_j^p = \frac{1}{n_p}\sum_{i \in I^p} x_{ij}.$$

These formulas defining $x^g$ and $x^p$ are used in step 304 to compute the average good profile $x^g$ and the average poor profile $x^p$.

The classifier adopted by Van 't Veer et al. and Van de Vijver et al. is the nearest mean classifier, using cosine correlation as its distance measure. Other classifiers and other distance measures may also be used. Such a classifier will classify a patient i to the good prognosis class if the distance of $x_i$ to $x^g$, denoted by $d(x_i, x^g)$, is smaller than the distance of $x_i$ to $x^p$, denoted by $d(x_i, x^p)$. From the definition of cosine distance it follows that a patient i with an expression vector $x_i$ may be classified as having a good prognosis if and only if $$d(x_i, x^g) < d(x_i, x^p) \qquad (1)$$

$$1 - \frac{x_i^T x^g}{\|x_i\|\|x^g\|} < 1 - \frac{x_i^T x^p}{\|x_i\|\|x^p\|}$$

$$x_i^T \left( \frac{x^g}{\|x^g\|} - \frac{x_i^p}{\|x^p\|} \right) > 0$$

$$x_i^T x^{diff} > 0,$$

where we define $$x^{diff} = \frac{x^g}{\|x^g\|} - \frac{x_i^p}{\|x^p\|}.$$

Note that the classification rule of equation 1 results in a linear classifier. However, the classifier used in Van 't Veer et al. is slightly different, as it is biased towards fewer false negatives, making it no longer linear. Such a non-linear classifier may also be used here. In step 306, a new sample (not coming from the training data set) is classified according to the classification rule of equation 1 ($x_i^T x^{dif} > 0$). Step 306 may be performed on a sample from a validation data set. It may also be performed during practical use of a classifier for classifying samples, for example to aid diagnosis of a patient.

To create a nearest mean classifier, a mean feature vector may be determined for each class. Such a mean feature vector of a particular class may be obtained by averaging a set of feature vectors known to be of that particular class. To use the nearest mean classifier to classify a new feature vector, the distance from the new feature vector to each of the mean feature vectors may be computed. The new feature vector may be classified according to the class of the mean feature vector having the smallest distance from the new feature vector.

For several reasons, classification as described above may be done not on the full feature set, but on a selected subset of features (or genes). For this, a procedure may be used that comprises two feature filtering steps, a feature ranking step and a classification evaluation step. As an example, one may start with a training set of 78 patients, each having reported expression levels on 24,481 genes.

Figure 4:
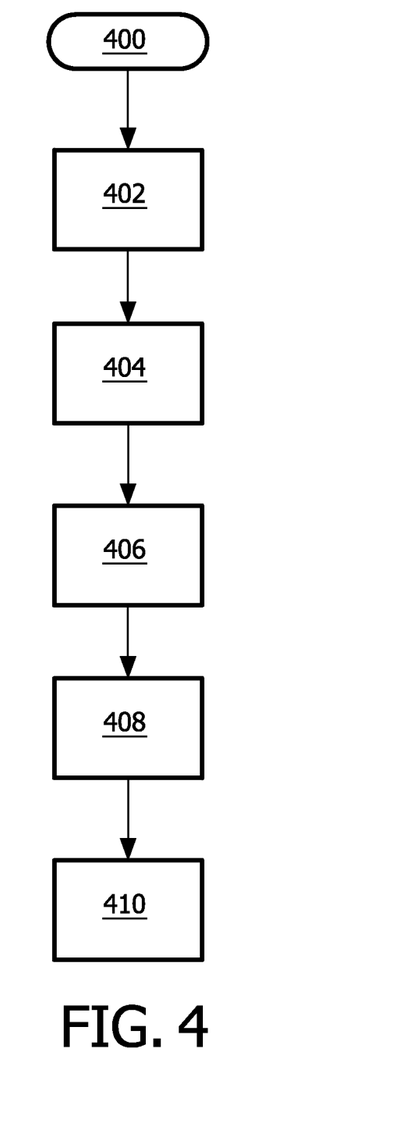
FIG. 4 is a flowchart illustrating a process of selecting an appropriate subset of features.

FIG. 4 illustrates a process of selecting an appropriate subset of features. In step 400, the process is initiated. The process proceeds as follows:

Step 402: Select only those features j that have at least a 2-fold change (i.e. $|x_{ij}| > \log_{10}(2) \approx 0.3$) and a P-value (the concept of P-value will be explained in detail hereinafter) smaller than 0.01, for more than 3 cases. In the example data set or 78 patients this may lead to a reduced set of 4,918 features.

Step 404: Select those features out of the ones selected in step 402 (4,918 features in the example) that have an absolute Pearson correlation with the class label of at least 0.3. In the example, this further reduced the set of features to a set of 231 features.

Step 406: Rank the features selected in step 404 (231 features in the example) by the absolute value of the Pearson correlation coefficient, starting from the highest to the lowest.

Step 408: Evaluate the nearest mean classifier, in a leave-one-out fashion (leave-one-out is a technique that is known in the art), using the top 5, top 10, top 15, etc. features as ranked in step 406. This step involves the training and evaluating classifiers based on the selected subsets of features using the process of FIG. 3.

Step 410: Select the subset of features evaluated in step 408 that results in the lowest total error rate. In the example data set, this turned out to be at 70 features.

In the example data set, the classifier using the top 70 features correctly predicts 65 out of the 78 class labels. In the process of FIG. 4, step 402 is the only step that includes information on the measurement noise.

A complicating factor in obtaining quantified gene expression information via microarrays is that there are a large number of different sources that may disturb the intensity measurement. In addition, the measurement error may be intensity dependent, e.g. higher intensity measurements may tend to have higher measurement. Note that many statistical tests implicitly assume measurement errors to be equal for each measurement. Microarray data often dramatically fail to meet this and other common statistical assumptions.

Some sources bias measurements in a systematic way and its direction is approximately predictable. Often it is possible to correct for these systematic effects by applying a set of suitable transformations. For instance, background corrections, normalization and dye-swap strategies may be developed to correct for systematic effects.

Error models may try to capture the random errors that may still be present after correction for the systematic errors. The exact value and direction of these errors may not be predictable, but the variability of the random error may follow certain rules that may be investigated. Error models can be constructed to capture the predictable behavior of this variance. Self-self hybridizations are frequently performed in order to aid the construction of error models. These are hybridizations in which the same mRNA source is hybridized to both channels, i.e., there is no differential expression and all non-zero log ratios are the effect of noise.

One of the error models that have been developed for microarray measurement data is the "Rosetta error model for gene expression analysis" by L. Weng et al., in Bioinformatics, 22(9):1111, 2006 (hereinafter: Rosetta). A detailed treatment of this model is beyond the scope of this description. For each individual intensity measurement I(i,j) the model provides an estimate on its variability $\sigma_{I(i,j)}$. As noted before, if the individual channel intensities are stochastic, the feature values $x_{ij}$ may be stochastic as well. The standard deviations of the individual channel intensities can be used to approximate the standard deviation of $x_{ij}$; see the Rosetta paper. After application of the Rosetta error model each measurement may be represented as a normally distributed stochast with mean $x_{ij}$ and standard deviation $\sigma_{ij}$, where $\sigma_{ij}$ represents the modeled noise information on the measurement $x_{ij}$.

When comparing two different samples, one may be careful not to attribute each non-zero log ratio to a difference in gene expression between the two samples, as some differences can be due to the measurement errors. It is possible to use $\sigma_{ij}$ to assign to each ratio $x_{ij}$ a so-called P-value, $p_{ij}$. This P-value is an indication of the probability of observing a value for the log ratio more extreme than $x_{ij}$ if the true log ratio is zero, while the measurement error is $\sigma_{ij}$. Thus $p_{ij}$ indicates whether a log ratio is significantly different from zero when taking the measurement error into account.

In order to analyze the effects of measurement noise, it would be preferable to have as detailed information as possible on it. Unfortunately, such information is not always available or published. For instance, in Van 't Veer et al., the only published noise information is in the form of P-values. Since the error model is known, it is still possible to deduce the spread on the log ratio for most instances, as for a normally distributed stochast $X_{ij}$ with mean zero and standard deviation $\sigma_{ij}$ the two sided P-value is given by $$p_{ij} = 2 \cdot Pr(X_{ij} > |x_{ij}|) =$$
$$2 \cdot (1 - Pr(X_{ij} \le |x_{ij}|)) = 2 \cdot \left(1 - Pr\left(\frac{X_{ij}}{\sigma_{ij}} \le \frac{|x_{ij}|}{\sigma_{ij}}\right)\right) = 2 \cdot \left(1 - cdf\left(\frac{|x_{ij}|}{\sigma_{ij}}\right)\right).$$

Herein, cdf is the cumulative distribution function of an N(0,1)-distributed random variable. Hence, if $x_{ij}$ and $p_{ij}$ are given, it is possible to compute $\sigma_{ij}$ by $$\sigma_{ij} = \frac{|x_{ij}|}{cdf^{-1}\left(1 - \frac{p_{ij}}{2}\right)}. \qquad (2)$$

Although equation 2 may provide the value of $\sigma_{ij}$ for most pairs of $x_{ij}$ and $p_{ij}$, in two cases it is not easy to deduce the value of $\sigma_{ij}$ using equation 2:

if $p_{ij}$ equals 1 the denominator of equation 2 will be zero and hence the outcome of the division in equation 2 is undefined, and if $x_{ij}$ equals zero, equation 2 always yields zero, regardless of the value $p_{ij}$.

In both cases $\sigma_{ij}$ may be set conservatively to zero. However that does not exclude other solutions. Furthermore, rounding effects may occur in situations with $p_{ij}$ close to one and/or $\sigma_{ij}$ close to zero. In some cases this can cause $\sigma_{ij}$ to be unrealistically high. In order to prevent such values from being generated a ceiling $\sigma_{max}$ to the value of $\sigma_{ij}$ may be applied.

The calculated noise information captured by $\sigma_{ij}$ may be used to generate modified expression levels from the original data. In order to perturb the gene expression data, some Gaussian noise with mean zero and standard deviation $\sigma_{ij}$ is added to each measurement $x_{ij}$, wherein $\sigma_{ij}$ is computed by equation 2. Note that in order to generate a new feature vector for a patient it has been implicitly assumed that the errors are independent and follow a normal distribution. However, the error distributions of different features may be dependent on each other. This dependence may be taken into account in the generation of modified expression levels in order to make the perturbations more realistic and to make the final classifications more accurate. Also note that the class labels are not altered, i.e. $L_i^{mod} = L_i$. New expression vectors may be generated via the following recipe:

$$x_{ij}^{mod} = x_{ij} + \varepsilon_{ij} \quad \text{with} \qquad (3)$$
$$\varepsilon_{ij}: N\left(\mu = 0, \sigma = \min\left\{\sigma_{max}, \frac{|x_{ij}|}{cdf^{-1}\left(1 - \frac{p_{ij}}{2}\right)}\right\}\right)$$

$\sigma_{max}$ may be used to avoid that the perturbations may become too large. For example, each sample may be replicated 1000 times using equation 3.

It is noted that the perturbations may have most effect if the original sample is near a boundary between two different classifications. Note that when some or all individual cases are affected by noise, the class means may be affected too. When this happens the decision boundary itself will be affected by the noise.

Figure 5:
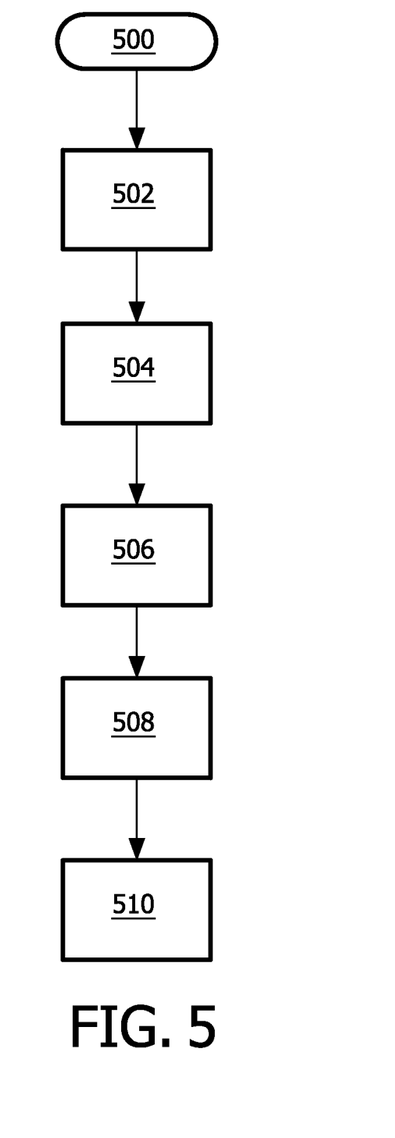
FIG. 5 is a flowchart illustrating a process of using measurement noise in individual features in a feature selection process.

FIG. 5 illustrates using the measurement noise in individual features in the feature selection process. In step 500 the feature selection process is initiated. In step 502, the genes that have a 2-fold change and a P-value smaller than 0.01 as in step 302 discussed above. In step 504, equation 3 is used to create, for each training sample i and feature j, a large number of modified expression vectors (for example 1000 modified expression vectors, yielding 1000 alternative training sets). These modified expression vectors may be referred to as perturbed replicas of the original measurement. In step 506, the Pearson correlation coefficient is calculated for each feature (or gene) with the (unaltered) class labels. For each gene (or feature) this gives a distribution of Pearson correlation coefficients. In step 508, the features are ordered by the absolute value of the average Pearson correlation over all replicas. Instead of using the average Pearson correlation over all replicas, other statistics could be used, for example the 25-percentile. The noise may impact the value of the correlation coefficient for all cases. In step 510, the subset of features is selected using the ordered features of step 508. Step 510 is similar to steps 408-410.

Using the feature noise in the feature selection step, for example using the process of FIG. 5, enables improved feature selection. Indirectly this improved feature selection has an effect on the classification of individual cases, since usually performing a classification based on different features may lead to different classification results. However, once the classifier has been trained, it is interesting to see how the feature noise of a new sample to be classified may impact the classification. It would be advantageous to use knowledge of the measurement error during the classification process, because this improves the accuracy (specificity and/or sensitivity) of the classification. Taking the measurement error into account during the classification may also enable to provide an indication of the certainty of a classification result.

Experiments have indicated that the number of deviating classifications due to noise perturbations may be higher if a small feature set is used. However, the noise may have some impact regardless of the number of features included in the classification. Also, in some experiments the impact of the noise is not monotonically decreasing with the number of features included in the classification. In some cases, adding more features helps to stabilize the classification, but at a certain number of features the classification begins to be impacted more by the noise again.

As discussed above, it is possible to replicate the feature vectors $x_i$ of the validation cases, while keeping $x^{dif}$ fixed. It is possible to estimate $x^{dif}$ from the training data. It is also possible to show the effect of the feature noise by perturbing the training set, thereby indirectly perturbing $x^{dif}$ while possibly maintaining a fixed (unperturbed) validation set. It is also possible to perturb both training and validation data sets. Herein, validation sets may be replaced with measured data of a sample used to actually test a sample for practical use (e.g. diagnosis of a patient). A deviating classification may be the result of a changing decision boundary. This decision boundary may have changed due to the perturbed training data. Perturbing of the training data also improves the classification accuracy, in particular when using small feature sets.

As explained in this text, feature noise may have an impact on both feature selection and classification. The many different transformations needed to create meaningful expression values make it difficult to analytically incorporate noise information. Perturbing expression levels via noise models circumvents these issues. In this text, the Rosetta error model was used to perturb the expression vectors. Although this model is quite general and can be applied to other microarray platforms, it is by no means the only existing error model. The existing alternatives may also be applied.

Experimentation using different classifiers reveals that other classifiers such as k-Nearest Neighbors, Support Vector Machines and Random Forests are affected by feature noise as well. The skilled person will appreciate that the techniques disclosed in this text (e.g. classification using perturbed replicas) may be applied to such classifiers.

The replicated data can be used as a means to regulate fitting procedures, e.g. to prevent overfitting. Instead of training with the original data it is possible to add many replicated data points and train a classifier using the larger training set. Such noise injection may be similar to Tikhonov regularization. For instance, local search methods focused on finding small feature subsets easily find many zero-error patterns in training data. These patterns, however, frequently do not validate well. It is to be expected that if a pattern fits the data purely by chance, a small perturbation already destroys the low-error classification result. If so, the error model, including perturbed replicas, may be used to filter out spurious patterns.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A classification system for classifying biomolecular data, comprising
   a processing device configured to process measurement data; and
   a non-transitory carrier having stored thereon a set of computer instructions for causing the processing device to execute a computer program, the computer program comprising:
      a statistical module for receiving measurement data comprising measurements of a plurality of numerical features of a sample to be classified and a plurality of respective error estimates of respective ones of the plurality of numerical features, and for associating respective probability density functions with the respective ones of the plurality of numerical features, wherein the respective probability density functions depend on the respective error estimates of the respective numerical features;
      a replication module for producing a plurality of perturbed replicas of the sample, the perturbed replicas comprising perturbed features, wherein each of the plurality of perturbed features is produced by randomly perturbing the respective ones of the plurality of numerical features according to the corresponding respective probability density functions;
      a classifier for classifying respective ones of the plurality of perturbed replicas based on the perturbed features and by applying predetermined classification criteria to obtain classified replicas, wherein each classified replica has one class of a plurality of classes associated therewith;
      an analyzer for classifying the sample to be classified based on a statistical analysis of a plurality of the classified replicas to obtain a sample classification.

2. The classification system according to claim 1, wherein the analyzer is arranged for computing a value indicative of a likelihood that the sample belongs to a particular class among the plurality of classes.

3. The classification system according to claim 2, wherein the analyzer is arranged for computing a plurality of likelihood values, wherein each respective likelihood value is indicative of a likelihood that the sample belongs to a respective particular class among the plurality of classes.

4. The classification system according to claim 1, wherein the analyzer ascertains a class associated with a largest number of perturbed replicas, and classifies the sample as belonging to the class having the largest number of perturbed replicas.

5. The classification system according to claim 1, wherein the respective probability density functions are respective normal distributions with respective standard deviations based on the error estimates, and wherein the replication module produces a value according to one of the respective normal distributions to obtain a perturbed feature.

6. The classification system according to claim 1, wherein the classifier comprises a nearest mean classifier.

7. The classification system according to claim 1, wherein the classifier is arranged for applying respective weights to respective ones of the plurality of numerical features of individual replicas based on the respective error estimates of the respective numerical features, wherein an influence of numerical features having a larger error estimate is reduced compared to an influence of numerical features having a smaller error estimate.

8. The classification system according to claim 1, wherein the input is arranged for receiving measurement data comprising at least one of:
gene expression data,
DNA transcript data, and
proteomics data.

9. The classification system according to claim 1, further comprising an assay-reader for providing the measurement data to the input.

10. The classification system according to claim 1, further comprising a clinical decision support system, wherein the clinical decision support system is arranged for receiving the sample classification and providing a diagnosis based on the sample classification.

11. The classification system according to claim 1, further comprising:
a training data set generator for generating a training data set, wherein the training data set generator is arranged for including a plurality of the replicas in the training data set; and
a training module for training the classifier on the training data set to obtain a trained classifier suitable for classifying a new sample and/or replicas of the new sample.

12. The system of claim 1, wherein the probability density function for at least one of the numerical features further depends on at least one error estimate of at least another one of the numerical features.

13. The system of claim 1, wherein the classifier classifies each of the respective ones of the plurality of perturbed replicas to one of the plurality of classes, and wherein the analyzer classifies the sample as belonging to a one of the classes to which the classifier classifies a largest number of the respective ones of the plurality of perturbed replicas.

14. The system of claim 1, wherein each of the plurality of classes has an average profile associated therewith and wherein the classifier: calculates a distance to each of a plurality of classes for each of the respective ones of the plurality of perturbed replicas; and classifies each of the respective ones of the plurality of perturbed replicas to a corresponding one of the plurality of classes to which the calculated distance for that perturbed replica is smallest.

15. A method of classifying biomolecular data, comprising
receiving at a processing device measurement data comprising measurements of a plurality of numerical features of a sample to be classified and a plurality of respective error estimates of respective ones of the plurality of numerical features;
associating respective probability density functions with the respective ones of the plurality of numerical features, wherein the respective probability density functions depend on the respective error estimates of the respective numerical features;
the processing device producing a plurality of perturbed replicas of the sample, the perturbed replicas comprising perturbed features, wherein the respective ones of the plurality of numerical features are randomly perturbed according to the corresponding respective probability density functions to obtain the perturbed features;
classifying respective ones of the plurality of perturbed replicas based on the perturbed features and by applying predetermined classification criteria to obtain classified replicas, wherein each classified replica has one class of a plurality of classes associated therewith;
classifying the sample to be classified based on a statistical analysis of the classified replicas to obtain a sample classification.

16. A non-transitory media having stored thereon computer program product comprising machine readable instructions for causing the processing device to perform the method according to claim 15.

17. The method of claim 15, wherein classifying the respective ones of the plurality of perturbed replicas based on the perturbed features comprises applying respective weights to respective ones of the plurality of numerical features of individual replicas based on the respective error estimates of the respective numerical features, wherein an influence of numerical features having a larger error estimate is reduced compared to an influence of numerical features having a smaller error estimate.

18. The method of claim 15, wherein the probability density function for at least one of the numerical features further depends on at least one error estimate of at least another one of the numerical features.

19. The method of claim 15, comprising:
classifying each of the respective ones of the plurality of perturbed replicas to one of the plurality of classes, and
classifying the sample as belonging to a one of the classes to which a largest number of the respective ones of the plurality of perturbed replicas is classified.

20. The method of claim 15, wherein each of the plurality of classes has an average profile associated therewith, the method comprising:
calculating a distance to each of a plurality of classes for each of the respective ones of the plurality of perturbed replicas; and
classifying each of the respective ones of the plurality of perturbed replicas to a corresponding one of the plurality of classes to which the calculated distance for that perturbed replica is smallest.

* * * * *